United States Patent [19]

Herbert

[11] 4,396,261

[45] Aug. 2, 1983

[54] METHOD FOR DETERMINING THE CURVATURE OF A CORNEA

[76] Inventor: M. Linton Herbert, 14255 Rosemary La., Apt. 8104, Largo, Fla. 33540

[21] Appl. No.: 213,608

[22] Filed: Dec. 5, 1980

[51] Int. Cl.³ .............................................. A61B 3/00
[52] U.S. Cl. ................................................ 351/247
[58] Field of Search ................... 351/39, 40, 13, 246, 351/247, 212

[56] References Cited

U.S. PATENT DOCUMENTS 4,019,813  4/1977  Cornsweet et al. ............. 351/40 X Primary Examiner—F. L. Evans
Attorney, Agent, or Firm—Cahill, Sutton & Thomas

[57] ABSTRACT

The method of the present invention uses a standard prior art refracting device of the type typically used by an optometrist to refract the human eye in air and in water. Computations utilizing the refraction data obtained during the air and water refraction measurements is used to compute the radius of curvature of the central area of the cornea of a human eye. The method of the present invention thereby substantially facilitates contact lens fitting procedures.

10 Claims, 5 Drawing Figures

METHOD FOR DETERMINING THE CURVATURE OF A CORNEA

BACKGROUND OF THE INVENTION

1. Field of the Invention

This invention relates to a process for determining the radius of curvature of the cornea of an eye, and more particularly, to a method for fitting contact lenses.

2. Description of the Prior Art

Prior art techniques for fitting a contact lens to the corneal surface of a human eye involve either trial and error techniques or the use of complicated and expensive devices. These available prior art devices are difficult to use and require a considerable amount of time to generate the desired cornea curvature data.

A prior art device known as a keratometer has the capability of measuring the radius of curvature of the cornea in a three to four millimeter diameter area in the vicinity of the pupil of the eye. The accuracy of measurements made by using a keratometer depend on the ability of a patent to properly focus his eye at a particular point.

In contact lens fitting procedures, one must determine the physical contour or shape of the rear surface of the contact lens so that the rear surface of the lens will have the same contour as the curved outer surface of the cornea itself. In addition, one must determine the optical characteristics of the lens which are required to compensate for the irregularities in the cornea.

The cornea of a human eye includes a centrally located optical zone which is positioned above the pupil of the eye. Light rays transmitted into the interior of the human eye pass through and are refracted by the optical zone of the eye. A corresponding optical zone in a contact lens is provided to obtain the required optical compensation for irregularities in the optical zone of the cornea. A contact lens also includes a bearing zone located concentrically around the optical zone, the lens bearing zone assists in securing the rear surface of the lens to the cornea of the eye and provides a bearing surface which supports the contact lens in front of the cornea.

Properly fitting a contact lens to a patient involves determining the proper contour of the rear surface of the optical zone of the lens as well as the contour of the rear surface bearing zone of the lens. Typical human corneas include an optical zone which can generally be approximated by a section of a sphere while the section of the cornea corresponding to the bearing zone of the lens has a flatter curvature.

The prior art discloses a variety of devices intended to determine the curvature of the cornea of an eye for the purpose of fitting contact lenses. U.S. Pat. No. 3,756,702 (Trachtman) discloses a method for producing precisely fitted contact lenses by generating an exact, enlarged photographic profile of the eye. This photographic profile of the eye is used to create a template for the curvature of the rear surface of a contact lens which precisely conforms to the shape of the cornea of the eye.

U.S. Pat. No. 3,285,512 (Reynolds) discloses a graphical corneal contact lens computer which permits a viewer to determine by superposition an appropriate contour for the rear surface of a contact lens which will approximately match the cornea curvature.

U.S. Pat. No. 3,510,207 (Neefe) discloses a method for fitting aspheric contact lenses. The Neefe method utilizes two different specialized lenses during his fitting procedure. The first lens includes an opaque area located at the center of the lens which occupies approximately half of the area of a dilated pupil. A second opaque lens includes a transparent aperture located at its center which also occupies half the area of a dilated pupil. Refractive measurements taken when an individual wears each of these two lenses assists in determining the shape of a contact lens.

U.S. Pat. No. 3,482,904 (Bolk) measures the eccentricity of a cornea by reflecting an image of a target from a predetermined area of the cornea which is viewed at an angle by a specialized telescopic instrument.

U.S. Pat. No. 3,937,566 (Townsely) discloses a method for producing contact lenses and involves the use of a keratometer.

SUMMARY OF THE INVENTION

It is therefore the primary object of the present invention to provide a method for determining the curvature of a cornea by using a commercially available refracting device to refract the cornea of an eye in air and in a transparent fluid to determine the curvature of the central area of the cornea.

Another object of the present invention is to provide a method for determining the curvature of a cornea which produces accurate results and an improved lens fit.

Yet another object of the present invention is to provide a method for determining the curvature of a cornea which substantially reduces trial and error contact lens fitting procedures.

Still another object of the present invention is to provide a method for determining the curvature of a cornea which does not require the use of highly specialized, complex equipment.

Briefly stated, the method of the present invention enables one to determine the curvature of the central area of the cornea of a human eye to simplify contact lens fitting procedures. The method of the present invention comprises the steps of determining the corrective refractive power of the eye in air and in a transparent fluid. After measuring the spacing between the refracting device utilized to obtain such refractive measurements and the anterior surface of the cornea, the refractive power of the cornea is determined by computation. Using the cornea refractive power, the radius of curvature of the cornea can then be computed. The contour of the bearing zone of the contact lens is determined by trial and error techniques.

DESCRIPTION OF THE DRAWINGS

The invention is pointed out with particularlity in the appended claims. However, other objects and advantages together with the operation of the invention may be better understood by reference to the following detailed description taken in connection with the following illustrations, wherein:

DESCRIPTION OF THE PREFERRED EMBODIMENT

In order to better illustrate the advantages of the invention and its contributions to the art, the process of the invention will now be described in some detail.

Figure 1:
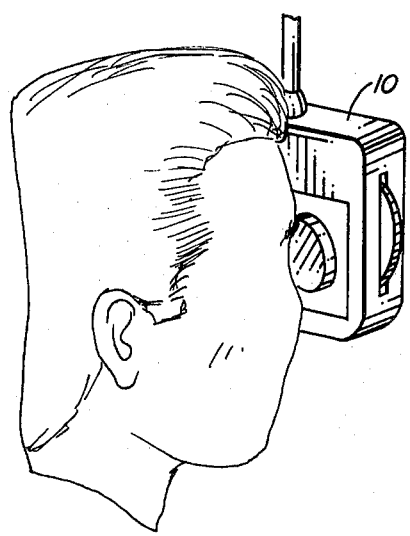
FIG. 1 is a perspective view illustrating a method of refracting the cornea of a human eye in air.
Figure 3:
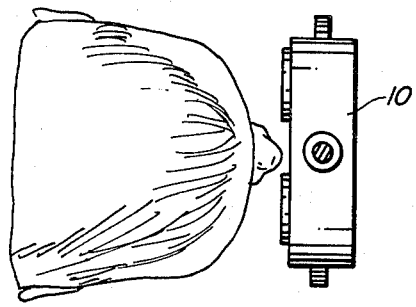
FIG. 3 is a view from above of the perspective view of FIG. 1.

FIGS. 1 and 3 illustrate that a standard refracting device 10 of the type typically used by optometrists and opthomologists is used to determine the corrective refractive power for each of an individual's corneas. If a cornea exhibits an astigmatic error, a second refractive measurement must be made on an axis perpendicular to the axis of the first measurement. These refractive measurements made with a cornea to air optical interface determine the strength and astigmatic corrections for the contact lens.

Figure 2:
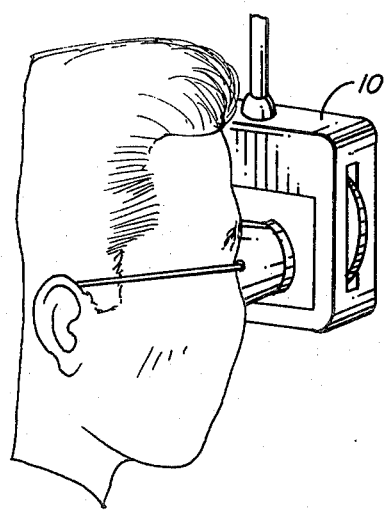
FIG. 2 is a perspective view illustrating the manner in which the cornea of the human eye is refracted while the cornea is immersed in a transparent fluid.
Figure 4:
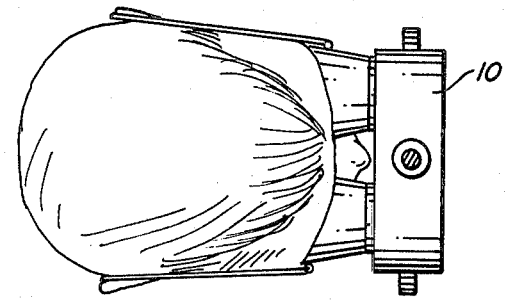
FIG. 4 is a view from above of the perspective view of FIG. 1.

FIGS. 2 and 4 illustrate that a second refractive measurement is made with the cornea immersed in a transparent fluid. The immersion of the cornea can readily be accomplished by having an individual don a pair of swimmer's goggles which include flat, optically transparent viewing ports. The goggles are filled with a fluid having an index of refraction approximately equal to the 1.336 index of refraction of the transparent medium within the aqueous humor of the human eye. Water, a saline solution, or a sugar solution are all satisfactory media. It has been found that a five percent sugar solution in water produces the least irritating transparent medium and actually permits the capillaries on the anterior surface of the cornea to absorb nutrients from the solution.

The eyepieces of the goggles can be filled with the transparent solution while the flat, transparent view ports are rested on the surface of a table. The individual then can bring his face down into the vicinity of the goggles and raise the goggles so that they contact his face and form a fluid tight seal. At this point the head strap for the goggles can be placed around the individual's head in a conventional manner to secure and maintain the goggles in position while maintaining a fluid tight interface with his face.

As is illustrated in FIGS. 2 and 4, standard refractive measurements are once again taken to determine the type and power of lens required to enable the individual to clearly see a chart positioned at a standard twenty-foot distance. It may be necessary to add a powerful auxiliary refracting lens to the refracting device to accomplish this step. While making the refractive measurements with the cornea 12 to fluid optical interface, it is not necessary to make a second measurement at a perpendicular angle to determine any astigmatic error induced by the cornea since the contact of the fluid with the cornea effectively eliminates the optical influence or power of the cornea. Since the index of refraction of the transparent corneal material and the index of refraction of the transparent fluid are very nearly the same, Snell's law indicates that a light ray will not be bent or refracted as it passes from the transparent fluid through the cornea and into the aqueous humor since the index of refraction of these three materials is virtually identical. The light ray will be refracted by crystaline lens 14, but this effect will be subtracted out in the mathematical equations to be discussed below.

Finally, the distance between refracting device 10 and the surface of cornea 12 and the distance between the surface of cornea 12 and the retina must be measured. This first distance can be determined by using a standard measuring device between the plane of refracting device 10 and the anterior surface of cornea 12. The distance between the anterior surface of the cornea and the retina can be measured by applying an ultra-sound transducer either to the surface of cornea 12 or to the exterior surface of a closed eyelid. If the ultra-sound transducer is positioned on a closed eyelid, the thickness of the eyelid can be subtracted from the measurement indicated by the ultra-sound device.

The symbols defined below will be used in mathematical computations which will be discussed shortly:

a. $R_c$—refractive power in diopters of the cornea in air;
b. $R_A$—corrective refractive power in diopters of the cornea measured by the refracting device in air;
c. $R_W$—corrective refractive power in diopters of the cornea measured by the refracting device when the cornea is immersed in the transparent fluid;
d. $f_W$—focal length in meters equivalent to the corrective refractive power of the eye in the transparent fluid ($f_W = 1/R_W$);
e. $r_c$—radius of curvature in meters of the cornea;
f. $f_c$—focal length in meters of the cornea in air ($f_c = 1/R_c$);
g. $L_{mc}$—linear distance in meters between the refractive measuring device and the anterior surface of the cornea;
h. $L_{mr}$—linear distance in meters between the refracting device and the retina of the eye;
i. $L_{cr}$—linear distance in meters between the surface of the cornea and the retina of the eye.

The measurements discussed above in connection with FIGS. 1 and 3 produce a value of $R_A$, while the measurements discussed above in connection with FIGS. 2 and 4 produce a value for $R_W$. $R_A$ and $R_W$ will be expressed as refractive powers in diopters. Since focal length $f = 1/R$, we have the following relationship:

$$f_w = 1/R_W$$

The refractive power of the cornea in air is indicated by the symbol $R_c$ and is defined by the following equation which was derived for use with the method of the present invention:

$$R_c = (R_W - R_A)[f_w/(f_w - L_{mc})] \qquad \text{Equation 1}$$

Standard text books on optics state the following equation for converting the focal length (f) of a plano-convex lens of a material with a refractive index of 1.336 into the radius of curvature (r) of that lens:

$$r = (f/4)$$

Since $f_c = 1/R_c$, the radius of curvature of the optical zone of the eye being examined is defined by the following relationship:

$$r_c = (f_c/4) = (1/4R_c) \qquad \text{Equation 2}$$

Figure 5:
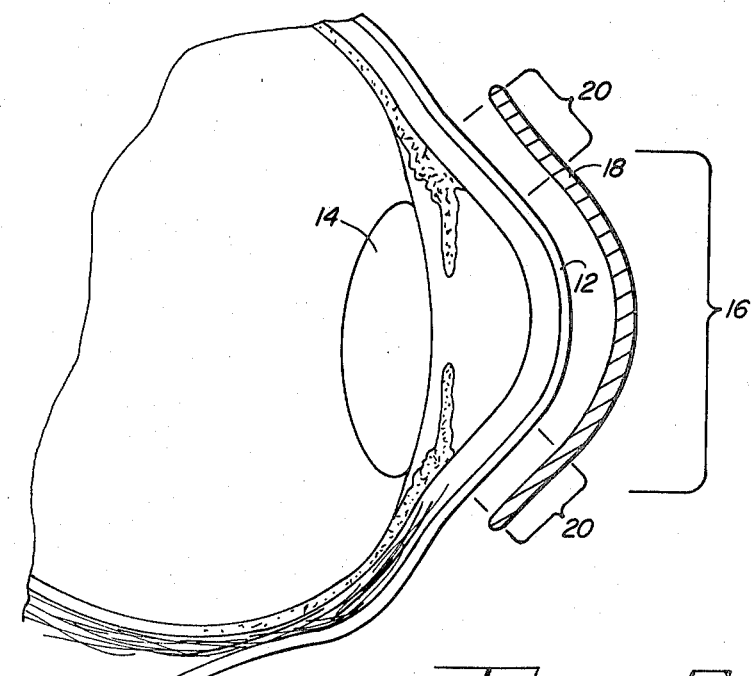
FIG. 5 is a partial sectional view of the anterior portion of a human eye, particularly illustrating the optical zone and bearing zone of the cornea and the optical zone and bearing zone of a contact lens intended to fit the cornea.

Equation 2 thus yields a value of $r_c$ which defines the radius of curvature of the surface of the optical zone of the cornea. The optical zone of cornea 12 and of contact lens 18 is indicated by reference number 16 in FIG. 5. The radius of curvature $r_c$ defines the contour of curvature of the rear portion of the contact lens so that it will precisely interface with the optical zone 16 of cornea 12. The standard refractive measurements taken in connection with the refraction of the eye in air then can be used to determine the thickness and curvature of the front surface of optical zone 16 of the contact lens.

The secondary or bearing zone of the contact lens is indicated generally by reference numbers 20 and 22. The rear surface of the bearing zone of contact lens 18 must be fitted by trial and error to the bearing zone of cornea 12. Since the shape of the rear surface of optical zone 16 of contact lens 18 has already been defined, the trial and error fitting procedure relating to the bearing zone of contact lens 18 will be substantially simplified.

As an alternative the following equation for $R_C$ can be utilized:

$$R_C = (R_W - R_A)(L_{mr}/L_{cr}) \qquad \text{Equation 3}$$

Equation 3 yields a close approximation to the result produced by Equation 1. However, using Equation 3 requires measuring the length of the eyeball by ultrasound in order to obtain the value of $L_{cr}$.

In practice one using the present invention could be provided with a chart or nomogram which would enable him to readily determine the value of $r_c$ (radius of curvature of the optical zone of the cornea) once values of $R_W$, $R_A$ and $L_{mc}$ are determined by measurement.

If there is astigmatic error in the cornea, then standard refraction will yield two values for $R_A$. Using the formulae above, one obtains two values of $r_c$. These are the two extreme values of radius of curve of the cornea. Either value, or an intermediate value may be selected for chosing a contact lens.

It will be apparent to those skilled in the art that the disclosed method for determining the curvature of a cornea may be modified in numerous ways and may assume many embodiments other than the preferred forms specifically set out and described above. Accordingly, it is intended by the appended claims to cover all such modifications of the invention which fall within the true spirit and scope of the invention.

I claim:

1. A method for determining the curvature of the central area of the cornea of a human eye to simplify contact lens fitting procedures, comprising the steps of:
   a. using a refracting device to determine the corrective refractive power of the eye in air;
   b. using said refracting device to determine the corrective refractive power of the eye in a transparent liquid;
   c. measuring the spacing between the anterior portion of the cornea and said refracting device;
   d. computing the refractive power of the cornea; and
   e. using the cornea refractive power to compute the cornea radius of curvature.

2. The method of claim 1 wherein the cornea includes a centrally located optical zone and a surrounding bearing zone, further comprising the step of selecting a contact lens having a curvature on the rear surface of the central area approximately equal to the radius of curvature of the optical zone of the cornea.

3. The method of claim 2 further comprising the step of selecting by trial and error a contact lens having a curvature on the rear surface of the bearing zone approximately equal to the curvature of the bearing zone of the cornea.

4. The method of claim 1 further comprising the step of positioning a liquid filled chamber having an optically flat transparent window on the end thereof over the eye to immerse the cornea in the transparent liquid.

5. The method of claim 4 wherein the interior of said chamber is filled with a transparent liquid having an index of refraction of approximately 1.336.

6. A method for determining the curvature of the central area of the cornea of a human eye to simplify contact lens fitting procedures, comprising the steps of:
   a. using a refracting device to determine the corrective refractive power of the eye in the air and in a transparent liquid;
   b. measuring the spacing between the anterior portion of the cornea and said refracting device and the spacing between the surface of the cornea and the retina of the eye;
   c. computing the refractive power of the cornea; and
   d. using the cornea refractive power to determine the radius of curvature of the central area of the cornea.

7. The method of claim 6 wherein the cornea includes a centrally located optical zone and a surrounding bearing zone, further comprising the step of selecting a contact lens having a curvature on the rear surface of the central area approximately equal to the radius of curvature of the optical zone of the cornea.

8. The method of claim 7 further comprising the step of selecting by trial and error a contact lens having a curvature on the rear surface of the bearing zone approximately equal to the curvature of the bearing zone of the cornea.

9. The method of claim 6 further comprising the step of positioning liquid filled goggles over the eye to immerse the cornea in the liquid.

10. The method of claim 9 wherein the space between said goggles and the eye is filled with a transparent liquid having an index of refraction of approximately 1.336.

* * * * *